(12) United States Patent
Van Egmond et al.

(10) Patent No.: US 7,396,972 B2
(45) Date of Patent: Jul. 8, 2008

(54) METHANOL FEED FOR PRODUCING OLEFIN STREAMS

(75) Inventors: Cor F. Van Egmond, Pasadena, TX (US); Michael Peter Nicoletti, Houston, TX (US); Eric D. Nelson, Houston, TX (US); Christopher D. W. Jenkins, South Caulfield (AU)

(73) Assignee: ExxonMobil Chemical Patents Inc., Houston, TX (US)

( * ) Notice: Subject to any disclaimer, the term of this patent is extended or adjusted under 35 U.S.C. 154(b) by 415 days.

(21) Appl. No.: 11/211,880

(22) Filed: Aug. 25, 2005

(65) Prior Publication Data

US 2007/0049647 A1    Mar. 1, 2007

(51) Int. Cl.
*C07C 1/00* (2006.01)
*C07C 27/00* (2006.01)

(52) U.S. Cl. ............. 585/640; 585/638; 585/639; 518/704; 518/715; 518/706

(58) Field of Classification Search ............ 518/704, 518/706, 715; 585/638–640
See application file for complete search history.

(56) References Cited

U.S. PATENT DOCUMENTS

| 4,720,557 | A | 1/1988 | Erdman | 549/368 |
|---|---|---|---|---|
| 6,248,794 | B1 | 6/2001 | Gieskes | 518/700 |
| 6,444,712 | B1 | 9/2002 | Janda | 518/706 |
| 6,486,219 | B1 | 11/2002 | Janda et al. | 518/706 |
| 2004/0116757 | A1 * | 6/2004 | Van Egmond et al. | 585/324 |

FOREIGN PATENT DOCUMENTS

| DE | 196 44 684 | 4/1998 |
|---|---|---|
| WO | WO 98/36038 | 8/1998 |

OTHER PUBLICATIONS

Song, Chunshan, "Tri-Reforming: A New Process Concept for Syngas Generation Using C0-2-Rich Natural Gas", American Institute of Chemical Engineers, [Spring National Meeting], New Orleans, LA, United States, Mar. 11-14, 2002 (2002), 3158-3166 Publisher: American Institute of Chemical Engineers, New York, N.Y. (Abstract).
Rusli, A., et al, "Nuclear Desalination for the Petrochemical Complex of the Natuna Project", Nuclear Desalination of Sea Water, Proceedings of an International Symposium on Desalination of Sea Water with Nuclear Energy, Taejon, S. Korea, May 26-30, 1997 (1997), 279-291 Publisher: International Atomic Energy Agency, Vienna, Austria (Abstract).
Sano, Hirosi, C02 Global Recycling Systems: via C02-Methanol or via C02-LNG?, Energy Conversion and Management (1995), 36(6-9), 895-8 (Abstract).
Derwent World Patents Index—Abstract—DE 19644684, Storage of Hydrogen in Liquid Form by Conversion to Methane, Methanol or Ethanol—is Described in Global Terms as a Means of Overcoming Difficulties of Storing Hydrogen Gas and Also Fixing the Greenhouse Gas CarbonDioxide, if only temporarily, with Special Benefits from Fuel Cell Conversion, Published Apr. 30, 1998.

* cited by examiner

*Primary Examiner*—Jafar Parsa (57) ABSTRACT

A method for producing an olefin stream is provided based on conversion of an initial natural gas stream into a synthesis gas. The resulting synthesis gas is enriched with $CO_2$ previously separated from the natural gas stream. The synthesis gas is then used to form a methanol composition, which can then be used as feedstock for a methanol-to-olefin conversion reaction.

34 Claims, 1 Drawing Sheet

FIG. 1

METHANOL FEED FOR PRODUCING OLEFIN STREAMS

FIELD OF THE INVENTION

This invention is for a method of forming a methanol feedstock and converting the methanol feedstock into olefins. More specifically, the methanol feedstock used in the olefin conversion is enriched with $CO_2$ separated from a natural gas stream.

BACKGROUND OF THE INVENTION

Methanol is one potential raw material that can be used for industrial oxygenate-to-olefin conversion reactions. Industrial scale production of olefins requires an abundant source of methanol or another oxygenate to provide the feedstock. U.S. Pat. Nos. 6,444,712 B1 and 6,486,219 B1 to Janda, disclose a method for producing olefins from methanol by way of using natural gas to make the methanol. The method includes converting the methane component of the natural gas to synthesis gas (syngas) using a steam reformer and a partial oxidation reformer. The syngas from each reformer is combined and sent to a methanol synthesis reactor. The combined syngas stream to the methanol synthesis reactor desirably has a syngas number of from about 1.4 to 2.6. The methanol product is then used as a feed in a methanol to olefin production process.

Gas reserves typically include other compounds, such as $CO_2$, that are separated from the natural gas prior to use. In some conventional processes, this $CO_2$ is considered a waste product that is vented to the atmosphere or otherwise disposed of. Other processes have attempted to use $CO_2$ as a source of carbon for other reactions. U.S. Pat. No. 6,248,794 describes a process where $CO_2$ separated from a natural gas stream is added with the natural gas stream into a reformer for producing synthesis gas. The synthesis gas is then fed into a reactor for conducting a Fischer-Tropsch reaction to create heavy hydrocarbons. Published application WO98/36038 describes a method for converting natural gas into methanol in a conversion plant where $CO_2$ recovered from the natural gas is recycled to the inlet stream of the conversion plant.

What is needed is a method for increasing or optimizing the efficiency of methanol production for use as feedstock for a methanol-to-olefin conversion process. The method should allow for improvement in the amount of methanol produced while minimizing the amount of cost required for additional equipment or raw materials. What is also needed is a method for reducing or eliminating the need to dispose of $CO_2$ found in gas reserves. The method should be environmentally friendly, leading to minimal or no release of greenhouse gases into the atmosphere. The method should also allow the $CO_2$ to be processed while adding a minimum of additional equipment.

SUMMARY OF THE INVENTION

This invention provides a process for forming an olefin stream. The process includes a step of separating a $CO_2$-containing stream from a natural gas stream. Preferably, the natural gas stream comprises at least 2 mol %, more preferably at least 5 mol %, $CO_2$. It is also preferred that the separated $CO_2$-containing stream comprise at least 75% $CO_2$ by weight.

A synthesis gas stream is formed from a second natural gas stream, and at least a portion of the separated $CO_2$-containing stream is added either to the second natural gas stream or to the synthesis gas stream. The synthesis gas stream is then contacted with a carbon oxide conversion catalyst to form a methanol composition. In one embodiment, the second natural gas stream is derived from the first natural gas stream.

In an embodiment of the invention, at least a portion of the separated $CO_2$-containing stream is added to the second natural gas stream. In another embodiment, at least a portion of the separated $CO_2$-containing stream is added into the synthesis gas stream. Preferably, at least 90% of the $CO_2$ in the separated $CO_2$-containing stream is added to the second natural gas stream or to the synthesis gas stream. Preferably, the synthesis gas stream is formed by steam reforming.

In a preferred embodiment, at least a portion of the separated $CO_2$-containing stream is added in a quantity to form the synthesis gas stream at a ratio M of at least 2.0, the ratio M being defined as $$M=([CO]+[H_2])/([CO]+[CO_2])$$

where [CO], [$H_2$], and [$CO_2$] represent the molar concentration of each compound. Preferably, M is from 2.05 to 2.5.

In an embodiment, at least 10% by weight of the $CO_2$ in the syngas stream, based on total weight of the syngas stream, is from the separated $CO_2$-containing stream. Preferably, from 15% to 22% by weight of $CO_2$ in the syngas stream, based on total weight of the syngas stream, is from the separated $CO_2$-containing stream.

In another embodiment, wherein the carbon oxide conversion catalyst is a nickel containing catalyst. Preferably, the carbon oxide conversion catalyst comprises at least one active metal or metal oxide of Group 6 or Group 8-10 of the Periodic Table of the Elements.

In one embodiment of the invention, the methanol composition is contacted with an olefin forming catalyst to form an olefin stream. The olefin forming catalyst is preferably a molecular sieve catalyst. More preferably, the molecular sieve is a silicoaluminophosphate molecular sieve.

In a further embodiment of the invention, an olefin stream is formed from the methanol and the olefin is contacted with a polyolefin forming catalyst to form a polyolefin. In yet another, at least a portion of the separated $CO_2$-containing stream is purified. Preferably, the at least a portion of the separated $CO_2$-containing stream comprises removing at least a portion of the sulfur-containing compounds in the separated $CO_2$-containing stream. More preferably, the purified $CO_2$-containing stream comprises 10 ppm or less of $H_2S$. Alternatively, the processes includes performing a hydrodesulfurization process on the second natural gas stream.

The elements of any two or more of the above described embodiments can be combined to describe additional embodiments of the invention.

DETAILED DESCRIPTION OF THE INVENTION

I. Introduction

This invention is directed to a method for making a methanol composition and using the methanol composition as a feedstock in an oxygenate to olefin conversion reaction. The method for making the methanol composition includes adding a $CO_2$-containing stream that was separated from a natural gas stream into a methanol production process. The $CO_2$- containing stream or flow is generated by separating the $CO_2$ stream from a natural gas stream during purification of the natural gas. A natural gas stream is then used to make synthesis gas. The natural gas stream that is reformed into synthesis gas can be derived from the natural gas stream that the $CO_2$ stream was separated from, or it can be an unrelated natural gas stream. At least a portion of the separated $CO_2$ stream or flow is then added into the synthesis gas.

Adding a $CO_2$ stream into the synthesis gas increases the amount of methanol that can be produced from the natural gas stream by providing an additional source of carbon. Additionally, because $CO_2$ is a greenhouse gas, many countries now regulate the amount of $CO_2$ that can be released into the atmosphere from a gas field. In embodiments where greater than 90% of the $CO_2$ is used to form methanol, the need for a separate and costly disposal technique (such as pumping the $CO_2$ back into the gas reserve) can be greatly reduced or eliminated. In a preferred embodiment, this invention provides a method for making a methanol composition by using the $CO_2$ from a natural gas reserve containing elevated levels of $CO_2$, such as greater than 10 mol % $CO_2$.

In another preferred embodiment, the $CO_2$ is separated from a natural gas stream that is reformed into synthesis gas, and at least a portion of the $CO_2$ is then added to the synthesis gas prior to making the methanol composition. More preferably, all of the $CO_2$ separated from the natural gas can be added to the synthesis gas prior to making the methanol composition. The methanol produced by this process is referred to as a methanol composition due to the potential presence of other compounds within the composition.

In still another preferred embodiment, a $CO_2$ stream is separated from a first natural gas stream that contains at least 2% by weight of $CO_2$, preferably at least 3.5% by weight of $CO_2$, more preferably at least 5% by weight of $CO_2$, and still more preferably at least 10% by weight of $CO_2$. At least 90% of the separated $CO_2$ stream is then added into a second natural gas stream. The second natural gas stream can be derived from the natural gas stream that the $CO_2$ stream was separated from, or the second natural gas stream can be an unrealted stream. The second natural gas stream, including the added $CO_2$, is passed through a hydrodesulfurization plant to remove sulfur impurities. The second natural gas stream is then used as a feedstock for a synthesis gas reforming reactor, such as a steam reforming reactor. The resulting synthesis gas can then be used for methanol formation, which can then be used as a feedstock for an oxygenate to olefin reactor.

In an embodiment, the method of the invention begins by providing a natural gas stream, such as a wellstream flow from a natural gas reserve. A $CO_2$ stream is then separated from the natural gas stream. The $CO_2$ stream is preferably at least 75% $CO_2$ by weight, more preferably at least 90% $CO_2$, and still more preferably at least 99% $CO_2$. After any other desired purification processes, the natural gas stream can be fed into a suitable reactor for forming synthesis gas. Alternatively, another natural gas stream can be fed into the reactor for forming synthesis gas. At least a portion of the separated $CO_2$ stream is then added back into the synthesis gas prior to feeding the synthesis gas into a methanol production reactor. Alternatively, a portion of the separated $CO_2$ can be added into the natural gas stream prior to forming synthesis gas, or portions of the separated $CO_2$ stream can be added at both locations.

In various embodiments, the portion of separated $CO_2$ added into the synthesis gas and/or added into the natural gas stream used for forming the synthesis gas is added to take advantage of excess hydrogen gas ($H_2$) present in the synthesis gas. For methanol production, the amount of CO, $CO_2$, and $H_2$ present in the synthesis gas can be characterized using the relation $$M=([CO]+[H_2])/([CO]+[CO_2])$$

where [x] represents the molar concentration of a compound. Values of M of 2.0 or greater are preferred for methanol production, with values greater than 2.0 indicating an excess of hydrogen in the synthesis gas. Preferably, the synthesis gas is formed using a reforming process that produces an excess of hydrogen gas, such as steam methane reforming. Based on the excess hydrogen, $CO_2$ is added to the synthesis gas and/or the natural gas so that the some or all of the excess hydrogen can be used for formation of additional methanol. Preferably, the amount of $CO_2$ added does not require further addition of hydrogen gas into the synthesis gas prior to producing methanol. In an embodiment, the amount of $CO_2$ added to the synthesis gas is 22 weight % or less of the feed gas used for formation of a methanol composition, or 20 weight % or less, or 15 weight % or less, or 10 weight % or less. In another embodiment, the amount of $CO_2$ added is 5 weight % or more, or 10 weight % or more, or 15 weight % or more. After producing the methanol composition, the methanol composition is fed into a methanol-to-olefin conversion reactor for production of olefins, such as ethylene and/or propylene.

II. Method for Separating $CO_2$ from Natural Gas

A natural gas reserve provides a suitable source of hydrocarbon feedstock for reforming into syngas, which can then be converted into methanol. Before using the natural gas as a feedstock for reforming, the natural gas can be processed to remove impurities from the gas flow, such as $CO_2$, $H_2S$, mercaptans, mercury, and heavy hydrocarbons. In an embodiment, a flow or stream of natural gas used as a hydrocarbon feedstock contains at least 2 mol % $CO_2$, or at least 3.5 mol % $CO_2$, or at least 5 mol % $CO_2$, or at least 7.5 mol % $CO_2$, or at least 10 mol % $CO_2$, or at least 12.5 mol % $CO_2$, or at least 15 mol % $CO_2$. In another embodiment, the natural gas flow contains 20 mol % or less of $CO_2$, or 17 mol % or less, or 14 mol % or less.

Any convenient process can be used for separating $CO_2$ from a natural gas stream. For example, $CO_2$ can be removed from the natural gas flow by contacting the natural gas with an amine and water. The $CO_2$ can then be separated from the amine using a tower, such as a regenerator tower. In an embodiment, the separated $CO_2$ comprises a $CO_2$-containing flow that has at least 75% $CO_2$ by weight, or at least 90% $CO_2$, or at least 99% $CO_2$.

A natural gas reserve can have widely varying ratios of the amount of $H_2S$ versus the amount of $CO_2$. In an embodiment, the molar ratio of $H_2S$ versus $CO_2$ present in a natural gas stream (or other hydrocarbon stream) before processing is at least 0.001, or at least 0.01, or at least 0.1, or at least 0.5. In another embodiment, the molar ratio of $H_2S$ to $CO_2$ is 6 or less, or 1 or less, or 0.5 or less. The amount of $H_2S$ and other sulfur compounds that are incorporated into the $CO_2$ stream will vary based on the amount of sulfur compounds in the natural gas stream as well as the specific details of the $CO_2$ separation process.

After forming the $CO_2$-containing stream or flow, the stream can be purified to remove other compounds. For example, if the $H_2S$ and/or mercaptan concentration in the $CO_2$ stream is greater than a few parts per million, the $CO_2$ stream can be further processed to remove these sulfur compounds. Any conventional equipment for this sulfur removing step can be utilized, such as a packed bed. Typically, a packed bed comprises a granular bed of zinc oxide such as 32-4 obtained from Katalco in ⅛ to 3/16 inch (3-5 mm) spheres can be used. System temperatures range between 200° C. and 500° C., and more preferably between 300° C. and 400° C. The space velocity through the bed should preferably be from 400 and 1000 standard cubic feet per hour per cubic feet of bed, and more preferably from 600 and 800 standard cubic feet per hour per cubic feet of bed. In an embodiment where the $CO_2$ flow is not further processed, the $CO_2$ flow has a concentration of at least one sulfur compound of 10 ppm or less, or 5 ppm or less, or 2 ppm or less. In another embodiment where the $CO_2$ flow is further processed to remove sulfur compounds, the $CO_2$ contains at least one sulfur compound with a concentration of 5 ppm or greater, or 10 ppm or greater, or 20 ppm or greater.

In an alternative embodiment, sulfur can be removed from either the hydrocarbon flow or the $CO_2$-containing flow using a selective amine unit. In such an embodiment, the hydrocarbon or $CO_2$-containing flow can be contacted with a selective amine and water. Preferably, the selective amine is composed of one or more sterically hindered amines, such as methyldiethanolamine or the hindered amines described in U.S. Pat. No. 4,405,585, which are commerically available as FLEXSORB® SE from ExxonMobil Research and Engineering Company. The sterically hindered amine will have a reduced rate of reaction with $CO_2$, and therefore will selectively react with sulfur compounds that are to be removed.

III. Method of Making a Methanol Composition

A. Examples of Methanol Synthesis Processes

A methanol composition can be manufactured from a variety of carbon sources. Examples of such sources include biomass, natural gas, $C_1$-$C_5$ hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In a preferred embodiment of this invention, natural gas is the hydrocarbon feed source. In such an embodiment, one or more natural gas sources can be used to provide both the hydrocarbon feed source and the $CO_2$ source used in creating a methanol feed for an oxygenate to olefin reaction.

One way of converting the carbon source to a methanol composition is to first convert the carbon source to synthesis gas (syngas), and then converting the syngas to the methanol composition. Any conventional process can be used. In particular, any conventional carbon oxide conversion catalyst can be used to convert the syngas to the methanol composition. In one embodiment, the carbon oxide conversion catalyst is a nickel containing catalyst.

Synthesis gas comprises carbon monoxide and hydrogen. Optionally, carbon dioxide and nitrogen are included. Conventional processes for converting carbon components to syngas include steam reforming, partial oxidation, and autothermal reforming.

The hydrocarbon feed stream used in the conversion of hydrocarbon to synthesis gas can be optionally treated to remove impurities that can cause problems in further processing of the hydrocarbon feed stream. For example, sulfur can be removed from the hydrocarbon feed stream by passing the feed stream through a hydrodesulfurization unit. These impurities can poison many conventional propylene and ethylene forming catalysts. A majority of the impurities, which may be present, can be removed in any conventional manner. The hydrocarbon feed is preferably purified to remove sulfur compounds, nitrogen compounds, particulate matter, other condensables, and/or other potential catalyst poisons prior to being converted into synthesis gas.

In one embodiment of the invention, the hydrocarbon feed stream is passed to a synthesis gas plant. Synthesis gas refers to a combination of hydrogen and carbon oxide produced in a synthesis gas plant from a hydrocarbon feed, the synthesis gas having an appropriate molar ratio of hydrogen to carbon oxide (carbon monoxide and/or carbon dioxide), as described below. The synthesis gas plant may employ any conventional means of producing synthesis gas, including partial oxidation, steam or $CO_2$ reforming, or some combination of these two chemistries. Preferably, the method of synthesis gas production results in a synthesis gas containing an excess of hydrogen gas.

Steam reforming generally comprises contacting a hydrocarbon with steam to form synthesis gas. The process preferably includes the use of a catalyst.

Partial oxidation generally comprises contacting a hydrocarbon with oxygen or an oxygen containing gas such as air to form synthesis gas. Partial oxidation takes place with or without the use of a catalyst, although the use of a catalyst is preferred. In one embodiment, water (steam) is added with the feed in the partial oxidation process. Such an embodiment is generally referred to as autothermal reforming.

Conventional synthesis gas-generating processes include gas phase partial oxidation, autothermal reforming, fluid bed synthesis gas generation, catalytic partial oxidation and various processes for steam reforming.

One method for characterizing synthesis gas is based on the stoichiometric ratio needed for synthesizing methanol from synthesis gas. As described above, the synthesis g as can be characterized by a ratio M, which is defined as

M=([CO]+[H$_2$])/([CO]+[CO$_2$])

where [x] represents the molar concentration of a compound. An M value of 2.0 or greater is preferred for synthesis of methanol from a synthesis gas, as such values represent a stoichiometric excess of hydrogen within the synthesis gas. Typically, a methanol plant will operate at an M value of 2.05 to suppress formation of by-products during methanol synthesis. A steam reforming process can be used to achieve M values of 2.5 to 3. More generally, an M of 2 can be achieved during reforming by using a reformer feed with a ratio of $CO_2/CH_4$ of 1:3.

B. Steam Reforming to Make Syngas

In the catalytic steam reforming process, hydrocarbon feeds are converted to a mixture of $H_2$, CO and $CO_2$ by reacting hydrocarbons with steam over a catalyst. This process involves the following reactions:

$$CH_4 + H_2O \leftrightarrows CO + 3H \quad (1)$$

or $$C_nH_m + nH_2O \leftrightarrows nCO + [n+(m/2)]H_2 \quad (2)$$

and $$CO + H_2O \leftrightarrows CO_2 + H_2 \quad (3) \text{ (shift reaction)}$$

The reaction is carried out in the presence of a catalyst. Any conventional reforming type catalyst can be used. The catalyst used in the step of catalytic steam reforming comprises at least one active metal or metal oxide of Group 6 or Group 8-10 of the Periodic Table of the Elements. The Periodic Table of the Elements referred to herein is that from *CRC Handbook of Chemistry and Physics*, 82$^{nd}$ Edition, 2001-2002, CRC Press LLC.

In one embodiment, the catalyst contains at least one Group 6 or Group 8-10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with least one promoter. Examples of promoters include alkali and rare earth promoters. Generally, promoted nickel oxide catalysts are preferred.

The amount of Group 6 or Group 8-10 metals in the catalyst can vary. Preferably, the catalyst includes from about 3 wt % to about 40 wt % of at least one Group 6 or Group 8-10 metal, based on total weight of the catalyst. More preferably, the catalyst includes from about 5 wt % to about 25 wt % of at least one Group 6 or Group 8-10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1% as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Gas hourly space velocity in the reformer should be sufficient for providing the desired CO to $CO_2$ balance in the synthesis gas. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, *Encyclopedia of Chemical Technology*, 3rd Ed., 1990, vol. 12, p. 951; and *Ullmann's Encyclopedia of Industrial Chemistry*, 5th Ed., 1989, vol. A-12, p. 186.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. Additionally, the amount of hydrogen contained in the synthesis gas can be increased by increasing the amount of steam used during reforming. On this basis, the mole ratio of steam to hydrocarbon feed in the conventional primary reformer unit is preferably at least about 1.5:1, or at least about 2:1, or at least about 2.5:1, or at least about 3:1. Alternatively, the mole ratio of steam to hydrocarbon feed in the conventional primary reformer unit is preferably 5:1 or less, or 4.5:1 or less, or 4:1 or less, or 3.5:1 or less.

The hydrogen to carbon oxide ratio of the synthesis gas produced will vary depending on the overall conditions of the reformer. In an embodiment, the molar ratio of hydrogen to carbon oxide in the synthesis gas will range from about 1:1 to about 5:1. In other embodiments, the molar ratio of hydrogen to carbon oxide will be at least about 2:1, or at least about 2.1:1, or at least about 2.2:1. In still other embodiments, the molar ratio of hydrogen to carbon oxide will be 3:1 or less, or 2.5:1 or less, or 2.3:1 or less.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

C. Partial Oxidation to Make Synthesis Gas

The invention further provides for the production of synthesis gas, or CO and $H_2$, by oxidative conversion (also referred to herein as partial oxidation) of hydrocarbon, particularly natural gas and $C_1$-$C_5$ hydrocarbons. According to the process, hydrocarbon is reacted with free-oxygen to form the CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m + (n/2)O_2 \leftrightarrows nCO + (m/2)H_2 \qquad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Ti, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Th, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminium titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) ratio of from about 1.2:1 to about 10:1. Preferably the feed and oxygen are injected into the reformer at a methane to oxygen ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about $10^3$ cm$^3$/g·hr to about $10^5$ cm$^3$/g·hr for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected by passing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction: $CO+H_2O \leftrightharpoons H_2 + CO_2$. This reaction occurs simultaneously with the oxidative conversion of the hydrocarbon in the feed to CO and $H_2$ or synthesis gas. The hydrocarbon used as feed in the partial oxidation process is preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon ratio in the range of from about 0.3:1 to about 0.8:1, more preferably, in the range of from about 0.45:1 to about 0.75:1. References herein to the oxygen-to-carbon ratio refer to the ratio of oxygen in the from of oxygen molecules ($O_2$) to carbon atoms present in the hydrocarbon feedstock. Preferably, the oxygen-to-carbon ratio is in the range of from about 0.45:1 to about 0.65:1, with oxygen-to-carbon ratios in the region of the stoichiometric ratio of 0.5:1, that is ratios in the range of from about 0.45:1 to about 0.65:1, being more preferred. When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

D. Combination Syngas Processes

Combination reforming processes can also be incorporated into this invention. Examples of combination reforming processes include autothermal reforming and fixed bed syngas generation. These processes involve a combination of gas phase partial oxidation and steam reforming chemistry.

The autothermal reforming process preferably comprises two synthesis gas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with air and residual hydrocarbons, and the mixed gas partial oxidized to carbon monoxides.

In another embodiment incorporating the autothermal reforming process, partial oxidation is carried out as the primary oxidating process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion.

In an alternative embodiment of the invention, a fixed bed syngas generation process is used to form synthesis gas. In the fixed bed syngas generation process, hydrocarbon feed and oxygen or an oxygen-containing gas are introduced separately into a fixed catalyst bed. Preferably, the catalyst is comprised of nickel and supported primarily on alpha alumina.

The fixed bed syngas generation process is carried out at conditions of elevated temperatures and pressures that favor the formation of hydrogen and carbon monoxide when, for example, methane is reacted with oxygen and steam. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

In one embodiment of the invention, methane, steam, and oxygen are introduced into a fluid bed by separately injecting the methane and oxygen into the bed. Alternatively, each stream is diluted with steam as it enters the bed. Preferably, methane and steam are mixed at a methane to steam molar ratio of from about 1:1 to about 3:1, and more preferably from about 1.5:1 to about 2.5:1, and the methane and steam mixture is injected into the bed. Preferably, the molar ratio of oxygen to methane is from about 0.2:1 to about 1.0:1, more preferably from about 0.4:1 to about 0.6:1.

In another embodiment of the invention, the fluid bed process is used with a nickel based catalyst supported on alpha alumina. In another embodiment, silica is included in the support. The support is preferably comprised of at least 95 wt % alpha alumina, more preferably at least about 98% alpha alumina, based on total weight of the support.

In one embodiment, a gaseous mixture of hydrocarbon feedstock and oxygen-containing gas are contacted with a reforming catalyst under adiabatic conditions. For the purposes of this invention, the term "adiabatic" refers to reaction conditions in which substantially all heat loss and radiation from the reaction zone are prevented, with the exception of heat leaving in the gaseous effluent stream of the reactor.

E. Enriching a Gas Stream with $CO_2$

In an embodiment, the synthesis gas is enriched with additional $CO_2$ after formation. The additional $CO_2$ added to the synthesis gas corresponds to the $CO_2$ stream separated from a natural gas source during purification of the natural gas. Adding $CO_2$ to the synthesis gas provides additional carbon, which can be used to form additional methanol if sufficient hydrogen gas is present in the synthesis gas. The $CO_2$ added to the synthesis gas can be a portion of the $CO_2$ stream as separated from the natural gas stream, or the $CO_2$ portion added to the synthesis gas can undergo one or more purification steps prior to addition. Preferably, more than 90% of a separated $CO_2$-containing stream is added into the synthesis gas.

In an alternative embodiment, $CO_2$ can be added to a natural gas stream prior to forming the synthesis gas. For example, a $CO_2$-containing stream can be added to a natural gas stream prior to passing the natural gas stream through a hydrodesulfurization process. In a preferred embodiment, more than 90% of a separated $CO_2$-containing stream is added into the natural gas stream.

If the separated $CO_2$ stream has a low sulfur content, such as 2 ppm or less of $H_2S$, or 5 ppm or less of $H_2S$, or 10 ppm or less of $H_2S$, the separated $CO_2$ stream can be added into the natural gas stream without additional purification. Alternatively, any sulfur in the $CO_2$ stream can be removed during processing of the natural gas stream prior to the reaction for forming synthesis gas, such as during a hydrodesulfurization process.

The amount of $CO_2$ added to the synthesis gas (or the natural gas stream prior to forming the synthesis gas) preferably does not require the addition of $H_2$ gas in order to maintain a stoichiometric excess of $H_2$. In an embodiment, the amount of $CO_2$ added results in a value of the ratio M for the synthesis gas of 2.0 or greater, or 2.1 or greater, or 2.2 or greater. In another embodiment, the amount of $CO_2$ added results in a value of the ratio M for the synthesis gas of 2.5 or less, or 2.4 or less, or 2.3 or less, or 2.2 or less.

F. Converting Syngas to Methanol

After being formed, the synthesis gas is sent to a methanol synthesis process and converted to a methanol composition. The methanol synthesis gas process is accomplished in the presence of a methanol synthesis catalyst.

In one embodiment, the synthesis gas is sent as is to the methanol synthesis process. In another embodiment, the hydrogen, carbon monoxide, and/or carbon dioxide content of the synthesis gas is adjusted for efficiency of conversion. Desirably, the synthesis gas input to the methanol synthesis reactor has a molar ratio of hydrogen ($H_2$) to carbon oxides ($CO+CO_2$) in the range of from about 0.5:1 to about 20:1, preferably in the range of from about 2:1 to about 10:1. In another embodiment, the synthesis gas has a molar ratio of hydrogen ($H_2$) to carbon monoxide (CO) of at least 2:1. Carbon dioxide is present in an amount of not greater than 50% by weight, based on total weight of the synthesis gas.

The $CO_2$ content, relative to that of CO, in the synthesis gas should be high enough so as to maintain an appropriately high reaction temperature and to minimize the amount of undesirable by-products such as paraffins. At the same time, the relative $CO_2$ to CO content should not be too high so as to reduce methanol yield. Desirably, the synthesis gas contains $CO_2$ and CO at a ratio of from about 0.5 to about 1.2, preferably from about 0.6 to about 1.0.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

The methanol synthesis catalyst is made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; and 5,385,949.

In one embodiment, the synthesis gas formed in the synthesis gas conversion plant is cooled prior to sending to the methanol synthesis reactor. Preferably, the synthesis gas is cooled so as to condense at least a portion of the water vapor formed during the synthesis gas process.

The methanol synthesis process used to manufacture the methanol composition of this invention can be any conventional process. Examples of such processes include batch processes and continuous processes. Continuous processes are preferred. Tubular bed processes and fluidized bed processes are particularly preferred types of continuous processes.

In general, the methanol synthesis process takes place according to the following reactions:

$CO+2H_2 \rightarrow CH_3OH$ $CO_2+3H_2 \rightarrow CH_3OH+H_2O$

The methanol synthesis process is effective over a wide range of temperatures. In one embodiment, the synthesis gas is contacted with the methanol synthesis catalyst at a temperature in the range of from about 150° C. to about 450° C., preferably in a range of from about 175° C. to about 350° C., more preferably in a range of from about 200° C. to about 300° C.

The process is also operable over a wide range of pressures. In one embodiment, the synthesis gas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities vary depending upon the type of continuous process that is used. Desirably, gas hourly space velocity of flow of gas through the catalyst bed is in the range of from about 50 $hr^{-1}$ to about 50,000 $hr^{-1}$. Preferably, gas hourly space velocity of flow of gas through the catalyst bed is in the range of from about 250 $hr^{-1}$ to about 25,000 $hr^{-1}$, more preferably from about 500 $hr^{-1}$ to about 10,000 $hr^{-1}$.

The methanol synthesis process produces a variety of hydrocarbons as by-products. According to the methanol composition of this invention, it is desirable to operate the process so as to maximize not only the amount of methanol formed, but also aldehydes and other alcohols which are particularly desirable in the conversion of oxygenates to olefins. In is particularly appropriate to maximize the amount of methanol formed in the methanol synthesis, and remove hydrocarbons less desirable in the conversion of oxygenates to olefins from the crude methanol product stream formed in the methanol synthesis reactor.

G. Refining the Methanol Composition

After reaction, the methanol composition can be used without further modification as a feedstock flow for an oxygenate to olefin reaction. Alternatively, the methanol composition can be further processed to modify the composition. Any conventional processing technique may be used, such as distillation, selective condensation, and/or selective adsorption. Process conditions, e.g., temperatures and pressures, can vary according to the particular methanol composition desired.

In one embodiment, the methanol composition from the methanol synthesis reactor is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another embodiment, the methanol composition from the methanol synthesis reactor is sent to a distillation system. The distillation system contains one or more distillation columns which are used to separate a desired methanol composition from water and hydrocarbon by-product streams. In an embodiment, the methanol composition that is separated from the crude methanol comprises a majority of the methanol and a majority of aldehyde and/or alcohol supplements contained in the crude alcohol prior to separation. In another embodiment, the methanol composition after distillation comprises a majority of the acetaldehyde and/or ethanol contained in the methanol composition prior to separation.

In one embodiment, the distillation system includes a step of treating the methanol steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

The invention can include any distillation system that produces a "fusel oil" stream (i.e., a stream having a majority of hydrocarbon compounds with a boiling point greater than that of methanol). It is especially advantageous when the fusel oil stream is liquid taken from a column fed with the crude methanol from the let-down vessel or with the bottoms liquid from a column fed with such crude methanol, the off-take point being at a level below the feed level. Alternatively or additionally, the fusel oil stream is taken from a level above the feed level in such a column. Because some of the higher alcohols are advantageous in the methanol composition of this invention, it is desirable to operate the distillation system to recover the $C_2$-$C_4$ alcohols along with the methanol rather than in the fusel oil stream.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles are taken overhead and methanol liquid as bottoms. The second is a "rectifying column" from which methanol product is taken as an overhead stream or at a high level, and water is removed as a bottoms stream. In this embodiment, the rectifying column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or rectifying column. The semi-crude methanol is passed to a rectifying column, from which methanol product is taken overhead or at a high level. Preferably, water or aqueous methanol is taken as a bottoms stream.

Alternatively, undesirable by-products are removed from the crude methanol stream from the methanol synthesis reactor by adsorption. In such a system, fusel oil can be recovered by regenerating the adsorbent.

IV. Description of the Methanol Composition

In an embodiment, the methanol composition provided to the methanol-to-olefin reaction system contains less than 99.85 wt % methanol, based on total weight of the composition. The methanol composition can also include additional oxygenates, such as alcohols and/or aldehydes. Preferably, the additional oxygenates are alcohols and/or aldehydes that have a boiling point not lower than that of formaldehyde, but not higher than that of butanol. In an embodiment, the methanol composition includes one or more additional oxygenates selected from the group consisting of ethanol, propanol, butanol, formaldehyde, acetaldehyde, proprionaldehyde, butyraldehyde, and valeraldehyde.

In an embodiment, the methanol composition comprises at least about 50 wt % methanol, based on total weight of the composition. Desirably, the methanol composition comprises at least about 75 wt % methanol, preferably at least about 80 wt % methanol, more preferably at least about 85 wt % methanol, and most preferably at least about 90 wt % methanol, based on total weight of the composition. In another embodiment of the invention, the methanol composition comprises not greater than 99 wt % methanol, based on total weight of the composition. Preferably, the methanol composition comprises not greater than 98 wt % methanol, more preferably not greater than 97 wt % methanol, and most preferably not greater than 96 wt % methanol, based on total weight of the composition.

In another embodiment, the methanol composition comprises 10 wppm or more, or 100 wppm or more, or 1,000 wppm or more, or 10,000 wppm or more, or 0.1 wt % or more of one or more alcohols, based on total weight of the composition. In such an embodiment, the one or more alcohols have a boiling point not lower than that of formaldehyde, but not higher than that of butanol. Preferably, the one or more alcohols are selected from the group consisting of ethanol, propanol and butanol.

In still another embodiment of the invention, the methanol composition comprises not greater than 15 wt % of the one or more alcohols, based on total weight of the composition, or not greater than 12 wt %, or not greater than 10 wt %, or not greater than 8 wt %.

In an embodiment of the invention, the methanol composition comprises 10 wppm or more, or 100 wppm or more, or 1,000 wppm or more, or 10,000 wppm or more, or at least 0.1 wt % of one or more aldehydes having a boiling point at least as high as that of formaldehyde, but not higher than that of butanol. In such an embodiment, the one or more aldehydes are selected from the group consisting of formaldehyde, acetaldehyde, proprionaldehyde, butyraldehyde, and valeraldehyde.

In another embodiment of the invention, the methanol composition comprises not greater than 15 wt % of the one or more aldehydes, based on total weight of the composition, or not greater than 12 wt %, or not greater than 10 wt %, or not greater than 8 wt %.

Although the methanol composition of this invention can include other components, the other components are included in a concentration such that the methanol composition remains suitable for contacting with an olefin forming catalyst to form an olefin stream. In one embodiment, the methanol composition further includes ketones, but in a concentration less than that of the one or more alcohols or the one or more aldehydes. Preferably the ketone concentration will be less than 50% that of the one or more alcohols or aldehydes, or less than 60%, or less than 70%. Examples of such ketones include one or more of acetone, methyl ethyl ketone, and any one or more of the pentanones. Preferably, the methanol composition includes not greater than 1 wt % ketones, or not greater than 0.1 wt % ketones, or not greater than 0.01 wt % ketones, based on total weight of the composition.

In another embodiment of the invention, the methanol composition includes ketones at a minimum concentration of 100 wppm, based on total weight of the composition. Preferably, the minimum concentration of ketones in the composition is 10 wppm, more preferably 1 wppm, and most preferably 0.01 wppm, based on total weight of the composition.

In yet another embodiment, the methanol composition includes water. The water content should not be of sufficient quantity to exert a positive partial pressure in the methanol to olefin conversion reaction, thereby increasing selectivity to ethylene and/or propylene. Desirably, the water content is at least about 0.1 wt %, based on total weight of the methanol composition. Preferably, the methanol composition contains at least about 0.5 wt % water, more preferably at least about 1.0 wt % water, and most preferably at least about 1.5 wt % water, based on total weight of the methanol composition.

In another embodiment, the methanol composition contains not greater than about 12 wt % water, based on total weight of the methanol composition. Preferably, the methanol composition contains not greater than about 10 wt % water, more preferably not greater than about 8 wt % water, and most preferably not greater than about 5 wt % water, based on total weight of the methanol composition.

In an optional embodiment of this invention, the methanol composition is converted to olefin along with other oxygenates or diluents. The additional oxygenates or diluents can be co-mixed with the methanol composition or added as a separate feed stream to an oxygenate conversion reactor. In one embodiment, the additional oxygenate is one or more alcohol(s), preferably aliphatic alcohol(s) where the aliphatic moiety of the alcohol(s) has from 1 to 10 carbon atoms, preferably from 1 to 5 carbon atoms, and most preferably from 1 to 4 carbon atoms. Ethanol is most preferred. The alcohols include lower straight and branched chain aliphatic alcohols and their unsaturated counterparts. Non-limiting examples of oxygenates include ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The methanol feed stream, in one embodiment, contains one or more diluent(s), typically used to reduce the concentration of the methanol, and are generally non-reactive to the oxygenates in the composition or to the molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to the methanol feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50 more percent, most preferably from about 5 to about 25 mole percent. In one embodiment, other hydrocarbons are added to the feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

V. Converting the Methanol Composition to Olefins

A. General Process Description

In one embodiment of the invention, the methanol composition is converted to olefins by contacting the methanol composition with an olefin forming catalyst to form the olefin product. The olefin product is recovered, and water, which forms during the conversion of the oxygenates in the methanol to olefins, is removed. After removing the water, the olefins are separated into individual olefin streams, and each individual olefin stream is available for further processing.

B. Oxygenate to Olefin Reaction Systems

Conventionally, oxygenate-to-olefin processes are carried out in a fluidized bed, fast fluidized bed, or riser reactor configuration where a fluid (gas) flow of a feedstock is passed through a bed of solid catalyst particles. The examples below describe an oxygenate to olefin reaction system that can be used to implement the processes of the claimed invention.

In an oxygenate to olefin reaction, a feed containing an oxygenate is contacted in a reaction zone of a reactor apparatus with a molecular sieve catalyst at process conditions effective to produce light olefins, i.e., an effective temperature, pressure, WHSV (weight hour space velocity) and, optionally, an effective amount of diluent, correlated to produce light olefins. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

The conversion of oxygenates to produce light olefins may be carried out in a variety of large scale catalytic reactors, including, but not limited to, fluid bed reactors and concurrent riser reactors as described in Fluidization Engineering, D. Kunii and O. Levenspiel, Robert E. Krieger Publishing Co. NY, 1977. Additionally, countercurrent free fall reactors may be used in the conversion process. See, for example, U.S. Pat. No. 4,068,136 and Fluidization and Fluid-Particle Systems, pages 48-59, F. A. Zenz and D. F. Othmer, Reinhold Publishing Corp., NY 1960.

In one embodiment of this invention, the gas and solid particles are flowed through the gas-solids reactor system at a weight hourly space velocity (WHSV) of from about 1 $hr^{-1}$ to about 5,000 $hr^{-1}$, preferably from about 5 $hr^{-1}$ to about 3,000 $hr^{-1}$, more preferably from about 10 $hr^{-1}$ to about 1,500 $hr^{-1}$, and most preferably from about 20 $hr^{-1}$ to about 1,000 $hr^{-1}$. In one preferred embodiment, the WHSV is greater than 25 $hr^{-1}$, and up to about 500 $hr^{-1}$. In this invention, WHSV is defined as the total weight per hour of the gas flowing between reactor walls divided by the total weight of the solids flowing between the same segment of reactor walls. The WHSV is maintained at a level sufficient to keep the catalyst composition in a fluidized state within a reactor.

In another embodiment of the invention directed toward use of cyclones in conjunction with a riser reactor, the gas and solid particles are flowed through the gas-solids reactor system at a gas superficial velocity (GSV) at least 1 meter per second (m/sec), preferably greater than 2 m/sec, more preferably greater than 3 m/sec, and most preferably greater than 4 m/sec. The GSV should be sufficient to maintaining the solids in a fluidized state, particularly in a fast fluidized state.

In still another embodiment, cyclones configured according to this invention can be used with a fixed fluidized bed reactor. In such an embodiment, the GSV can be as low as 0.03 m/s.

In yet another embodiment of the invention, the solids particles and gas are flowed through the gas-solids reactor at a solids to gas mass ratio of about 5:1 to about 75:1. Preferably, the solids particles and gas are flowed through the gas-solids reactor at a solids to gas mass ratio of about 8:1 to about 50:1, more preferably from about 10:1 to about 40:1.

In one practical embodiment, the process is conducted as a fluidized bed process or high velocity fluidized bed process utilizing a reactor system, a regeneration system and a recovery system. In such a process the reactor system conveniently includes a fluid bed reactor system having a first reaction region consisting of various fast fluid or dense fluid beds in series or parallel and a second reaction region within at least one disengaging vessel, comprising two or more cyclones configured and/or operated according to various embodiments of the invention. In one embodiment, the fast fluid or dense fluid beds and disengaging vessel are contained within a single reactor vessel. Fresh feedstock, preferably containing one or more oxygenates, optionally with one or more diluent (s), is fed to the one or more fast fluid or dense fluid beds reactor(s) into which a molecular sieve catalyst composition or coked version thereof is introduced. In one embodiment, prior to being introduced to the reactor(s), the molecular sieve catalyst composition or coked version thereof is contacted with a liquid and/or vapor, preferably water and methanol, and a gas, for example, an inert gas such as nitrogen.

In an embodiment, the amount of fresh feedstock fed as a liquid and/or a vapor to the reactor system is in the range of from 0.1 weight percent to about 99.9 weight percent, such as from about 1 weight percent to about 99 weight percent, more typically from about 5 weight percent to about 95 weight percent based on the total weight of the feedstock including any diluent contained therein. The liquid and vapor feedstocks may be the same composition, or may contain varying proportions of the same or different feedstocks with the same or different diluents.

The process of this invention can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the process of this invention can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

In embodiments involving a riser reactor, the solids particles and gas are flowed through the gas-solids reactor at a solids to gas mass ratio of about 0.5:1 to about 75:1. Preferably, the solids particles and gas are flowed through the gas-solids reactor at a solids to gas mass ratio of about 8:1 to about 50:1, more preferably from about 10:1 to about 40:1.

During the conversion of a hydrocarbon feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

The feedstock entering the reactor system is preferably converted, partially or fully, in a reaction region into a gaseous effluent. In an embodiment, the reaction region is closely coupled to a plurality of separation devices, such as cyclone separators. In another embodiment, the gaseous effluent enters a disengaging vessel along with the coked catalyst composition. In such an embodiment, the disengaging vessel includes cyclone separators configured and/or operated according to the invention. In still another embodiment, the disengaging vessel also includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition. After exiting the separation devices and/or disengaging vessels, some or all of the catalyst can then introduced to a regeneration system.

In an embodiment, at least a portion of the coked catalyst composition is withdrawn from one or more of the disengaging vessels and introduced to the regeneration system. The regeneration system comprises a regenerator where the coked catalyst composition is contacted with a regeneration medium, preferably a gas containing oxygen, under conventional regeneration conditions of temperature, pressure and residence time. In an embodiment, a gas-solids flow exiting a regenerator may be passed through cyclones configured according to the invention. Alternatively, at least a portion of the catalyst can be flowed to bypass the regeneration system. The catalyst bypassing the regenerator can be flowed to another desired portion of the reaction system, such as flowing the catalyst directly into a catalyst cooler or allowing the catalyst to rejoin a fluidized bed in the reactor.

Non-limiting examples of suitable regeneration media include one or more of oxygen, $O_3$, $SO_3$, $N_2O$, $NO$, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to about 700° C. The regeneration pressure may be in the range of from about 15 psia (103 kpaa) to about 500 psia (3448 kpaa), such as from about 20 psia (138 kpaa) to about 250 psia (1724 kpaa), including from about 25 psia (172 kPaa) to about 150 psia (1034 kPaa), and conveniently from about 30 psia (207 kPaa) to about 60 psia (414 kpaa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture).

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the reactor(s). In one embodiment, the regenerated catalyst composition withdrawn from the regeneration system is returned to the reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, 1997 (336-337).

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous reactor effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene (C2) splitter, propylene (C3) splitter and butene (C4) splitter.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Typically, in converting one or more oxygenates to olefin(s) having 2 or 3 carbon atoms, a minor amount hydrocarbons, particularly olefin(s), having 4 or more carbon atoms is also produced. The amount of $C_4+$ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products.

C. Description of Olefin Forming Catalyst

In an embodiment, the apparatus and method of the invention are generally useful for separating any solid particles in a gas-solids flow. In another embodiment, the solid particles can be catalyst particles, such as molecular sieve catalyst particles.

Molecular sieve catalyst particles for use in a gas-solids reaction can be synthesized by a variety of methods. In an embodiment, catalyst particles are synthesized by combining a first dried molecular sieve catalyst with water to make a water-catalyst composition, making a slurry from the water-catalyst composition, and drying the slurry to produce a second dried molecular sieve catalyst. The method particularly provides for the re-manufacturing, recycling or re-working of dried or substantially dried, or partially dried molecular sieve catalysts to yield catalyst particles with properties that are acceptable to the user or manufacturer. Such properties are usually observed after the dried molecular sieve catalyst is calcined. These properties include acceptable particle size, particle size distribution, particle density, and particle hardness.

The catalysts of this invention can include any of a variety of molecular sieve components. The components include zeolites or n on-zeolites, preferably non-zeolites. In one embodiment, the molecular sieves are small pore non-zeolite molecular sieves having an average pore size of less than about 5 angstroms, preferably an average pore size ranging from about 3 to 5 angstroms, more preferably from 3.5 to 4.2 angstroms. These pore sizes are typical of molecular sieves having 8 membered rings.

Conventional crystalline aluminosilicate zeolites having catalytic activity are desirable molecular sieves that can be used in making the catalyst of this invention. Examples of such zeolite materials are described in U.S. Pat. Nos. 3,660,274 and 3,944,482, both of which are incorporated herein by reference. Non-limiting examples of zeolites which can be employed in the practice of this invention, include both natural and synthetic zeolites. These zeolites include zeolites of the structural types included in the *Atlas of Zeolite Framework Types*, edited by Ch. Baerlocher, W. M. Meier, D. H. Olson, Fifth Revised edition, Elsevier, Amsterdam, 2001.

Zeolites typically have silica-to-alumina ($SiO_2/Al_2O_3$) mole ratios of at least about 2, and have uniform pore diameters from about 3 to 15 Angstroms. They also generally contain alkali metal cations, such as sodium and/or potassium and/or alkaline earth metal cations, such as magnesium and/or calcium. In order to increase the catalytic activity of the zeolite, it may be desirable to decrease the alkali metal content of the crystalline zeolite to less than about 5 wt. %, preferably less than about 1 wt. %, and more preferably less than about 0.5 wt. %. The alkali metal content reduction, as is known in the art, may be conducted by exchange with one or more cations selected from the Groups IIB through VIII of the Periodic Table of Elements (the Periodic Table of Elements referred to herein is given in *Handbook of Chemistry and Physics*, published by the Chemical Rubber Publishing Company, Cleveland, Ohio, 45th Edition, 1964 or 73rd Edition, 1992), as well as with hydronium ions or basic adducts of hydronium ions, e.g., $NH_4^+$, capable of conversion to a hydrogen cation upon calcination. Desired cations include rare earth cations, calcium, magnesium, hydrogen and mixtures thereof. Ion-exchange methods are well known in the art and are described, for example, in U.S. Pat. Nos. 3,140,249; 3,142,251 and 1,423,353.

In another embodiment, the catalyst particles which are flowed through the gas-solids reactor system of this invention are molecular sieve catalysts, such as a conventional molecular sieve. Examples include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice*, Second Completely Revised and Expanded Edition, Volume 137, pages 1-67, Elsevier Science, B. V., Amsterdam, Netherlands (2001).

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161

489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. Pat. No. 6,743,747 (integrated hydrocarbon co-catalyst), PCT WO 01/64340 published Sep. 7, 2001 (thorium containing molecular sieve), and R. Szostak, Handbook of Molecular Sieves, Van Nostrand Reinhold, New York, N.Y. (1992).

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO molecular sieves useful herein include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56 and metal containing molecular sieves thereof. Of these, particularly useful molecular sieves are SAPO-18, SAPO-34, SAPO-35, SAPO-44, SAPO-56 and metal containing derivatives thereof. SAPO-34 is particularly preferred.

In another embodiment of the invention, the catalyst used in this invention incorporates aluminophosphate (AlPO) molecular sieves. These molecular sieves can be included as separate crystals or they can be intermixed with other crystalline structures such as by an intergrowth structure. Examples of aluminophosphates include AlPO-5, AlPO-11, AlPO-18, AlPO-31, AlPO-34, AlPO-36, AlPO-37 and AlPO-46.

In one embodiment, the catalyst includes a combination of at least one SAPO and at least one AlPO molecular sieve, wherein the SAPO is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47 and SAPO-56, and the AlPO is selected from the group consisting of AlPO-5, AlPO-11, AlPO-18, AlPO-31, AlPO-34, AlPO-36, AlPO-37 and AlPO46. The sieves can be combined as separate crystals or as intergrown crystals. Preferably, the SAPO is SAPO-18 or SAPO-34, and preferably, the AlPO is AlPO-34 or AlPO-18.

Additional examples of intergrowth molecular sieves useful in this invention include those described in U.S. Patent Application Publication No. 2002-0165089 and International Publication No. WO 98/15496, published Apr. 16, 1998. Note that SAPO-18, AlPO-18 and RUW-18 have an AEI framework-type, and SAPO-34 has a CHA framework-type, and that preferred molecular sieves used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

VI. Olefin Product Recovery and Use

In one embodiment, olefin product and other gases are withdrawn from the reactor and are passed through a recovery system. Any conventional recovery system, technique and/or sequence useful in separating olefin(s) and purifying olefin(s) from other gaseous components can be used in this invention. Examples of recovery systems include one or more or a combination of various separation, fractionation and/or distillation towers, columns, and splitters, and other associated equipment; for example, various condensers, heat exchangers, refrigeration systems or chill trains, compressors, knockout drums or pots, pumps, and the like.

Non-limiting examples of distillation towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Various recovery systems useful for recovering predominately olefin(s), preferably prime or light olefin(s) such as ethylene, propylene and/or butene are described in U.S. Pat. Nos. 5,960,643, 5,019,143, 5,452,581 and 5,082,481, 5,672,197, 6,069,288, 5,904,880, 5,927,063, and 6,121,504, 6,121,503, and 6,293,998.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology, 4th Edition*, Volume 9, John Wiley & Sons, 1996, pages 249-271 and 894-899. Purification systems are also described in for example, U.S. Pat. Nos. 6,271,428, 6,293,999, and U.S. patent application Ser. No. 09/689,363 filed Oct. 20, 2000.

The ethylene and propylene streams produced and recovered according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4$+ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4$+ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

VII. Example of a System for Converting Natural Gas to Olefins

Figure 1:
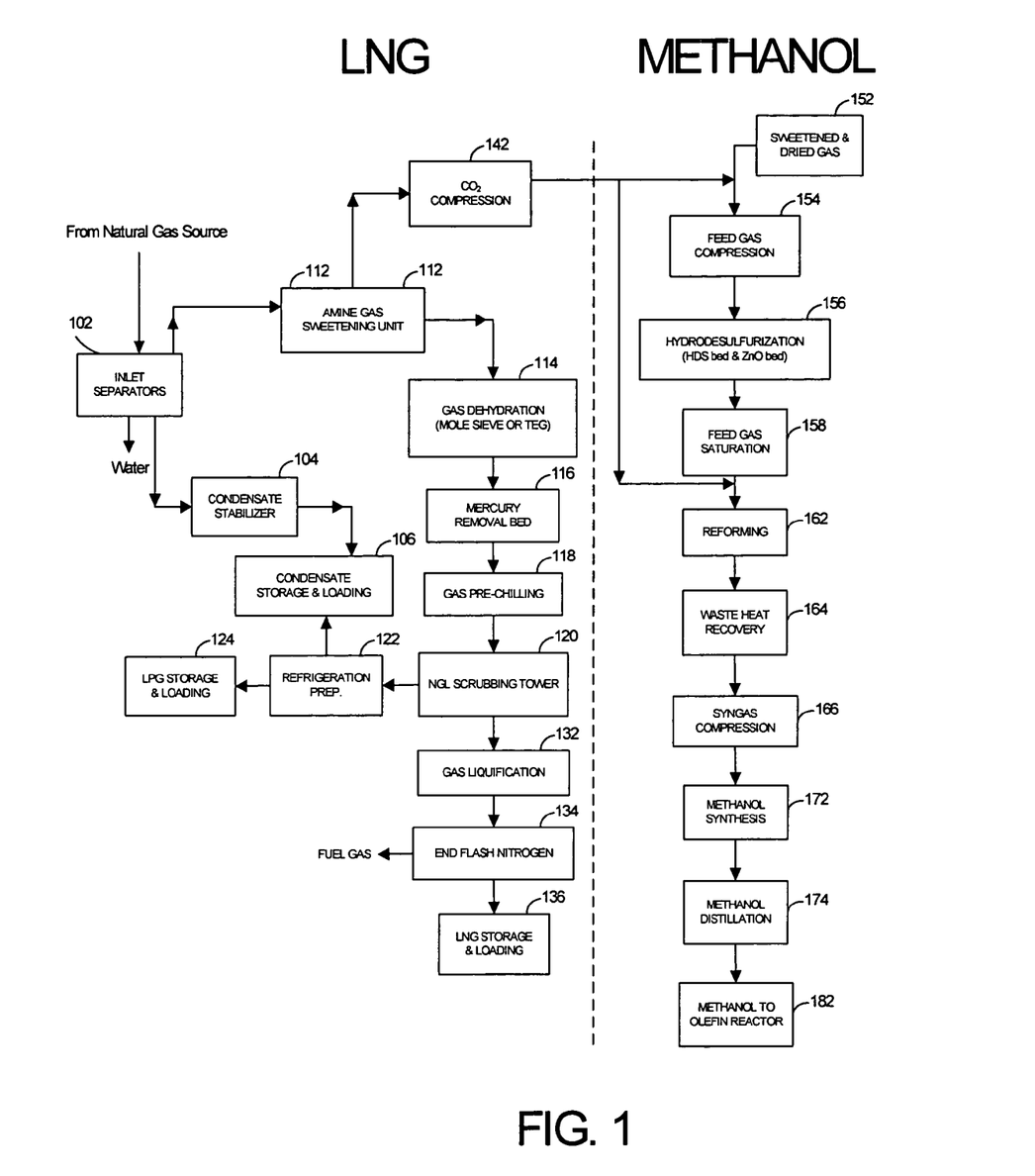
FIG. 1 schematically shows a processing apparatus for producing olefins according to an embodiment of the invention.

FIG. 1 shows a process flow for starting with a natural gas source, separating out $CO_2$ as well as impurities in the natural gas, forming a synthesis gas from the natural gas, enriching the synthesis gas with at least a portion of the separated $CO_2$, creating a methanol composition from the synthesis gas, and then converting the methanol composition into olefins.

In FIG. 1, a wellstream fluid from a natural gas reserve is fed into inlet separators 102. The inlet separators separate the wellstream fluid into water, a condensate stream, and a natural gas stream. The condensate stream is composed of heavier components, such as longer chain hydrocarbons. The condensate stream is fed into a condensate stabilizer 104 prior to passing the condensate into storage 106. The natural gas stream flows into an amine gas sweetening unit 112, where $CO_2$ is separated out from the natural gas stream. Depending on the amine used, some sulfur compounds may be separated out into the $CO_2$ stream. The natural gas stream is then passed into a gas dehydration unit 114 to remove excess water. A mercury removal bed 116 is then used to remove mercury from the natural gas stream. The natural gas stream is then chilled in a cooling unit 118 prior to being passed into scrubbing tower 120 for removal or separation of propane and other condensates. The stream of condensates and propane produced by scrubbing tower 120 is passed through a refrigeration unit 122, with the condensates being sent to condensate storage 106 and the propane being sent to liquid propane storage 124. The natural gas stream emerging from scrubbing tower 120 is passed to a gas liquefier 132. After liquefication, any remaining gases in the liquid are separated out in flash nitrogen rejector 134. The resulting liquefied natural gas can then either be stored 136 for later use, or it can be immediately passed on to feed storage 152 for use in methanol production (connection not shown).

In the methanol production process, a liquefied natural gas stream is recombined with at least a portion of the $CO_2$ separated out by amine gas sweetening unit 112. After separation, the $CO_2$ stream (or at least a portion of the $CO_2$ stream)

is passed through a $CO_2$ compressor 142 prior to being reintroduced into the natural gas stream. The combined natural gas and $CO_2$ stream is then fed to a feed gas compressor 154. After compression, the combined stream is passed through a hydrodesulfurizer 156 to remove any remaining sulfur containing compounds. The feed gas is then saturated with steam in saturator 158 prior to passing the feed gas into a reformer 162. If less than all of the available $CO_2$ stream was added into the natural gas stream prior to feed gas compression, additional $CO_2$ can be added to the synthesis gas at this point. Reformer 162 then converts the feed gas into synthesis gas. The converted synthesis gas is passed through a heat exchanger 164 in order to recover heat, and then the synthesis gas is passed through a compressor 166. In an alternative embodiment (not shown), the $CO_2$ stream from $CO_2$ compressor 142 can be added to the synthesis gas after it leaves reformer 162, or $CO_2$ can be added to both the natural gas stream before reforming as well as the synthesis gas after reforming. The synthesis gas is then passed into a methanol conversion unit 172 to form methanol. The methanol composition produced can be optionally purified, such as by passing through a distillation unit 174. The methanol produced is then fed to a methanol to olefin reactor 182 for production of desired olefins, such as ethylene and propylene.

The principles and modes of operation of this invention have been described above with reference to various exemplary and preferred embodiments. As understood by those of skill in the art, the overall invention, as defined by the claims, encompasses other preferred embodiments not specifically enumerated herein.

We claim:

1. A process for forming an olefin stream, the process comprising:
   (a) separating a $CO_2$-containing stream from a first natural gas stream, the natural gas stream comprising at least 2 mol % $CO_2$ and the $CO_2$-containing stream comprising at least 75% $CO_2$ by weight;
   (b) reforming a second natural gas stream to form a synthesis gas stream;
   (c) adding at least a portion of the separated $CO_2$-containing stream into the synthesis gas stream;
   (d) contacting the synthesis gas stream with a carbon oxide conversion catalyst to form a methanol composition comprising:
      i. at least 50 wt % and less than 99.85 wt % methanol, based on total weight of the methanol composition,
      ii. greater than 10 wppm and not greater than 15 wt % ethanol, based on total weight of the methanol composition, and
      iii. greater than 10 wppm and not greater than 15 wt % acetaldehyde, based on total weight of the methanol composition; and
   (e) contacting the methanol composition with an olefin forming catalyst to form an olefin stream comprising greater than 65 wt % ethylene and propylene.

2. The process of claim 1, wherein the second natural gas stream is derived from the first natural gas stream.

3. The process of claim 1, wherein reforming the second natural gas stream comprises steam reforming of the second natural gas stream.

4. The process of claim 1, wherein the at least a portion of the separated $CO_2$-containing stream is added to the synthesis gas stream so that the synthesis gas stream has a value of a ratio M of at least 2.0, the ratio M being defined as $$M=([CO]+[H_2])/([CO]+[CO_2])$$

where [CO], [$H_2$], and [$CO_2$] represent the molar concentration of each compound.

5. The process of claim 4, wherein the at least a portion of the separated $CO_2$-containing stream is added to the synthesis gas stream so that the value of M for the synthesis gas stream is from 2.05 to 2.5.

6. The process of claim 1, wherein adding at least a portion of the separated $CO_2$-containing stream into the synthesis gas stream comprises adding at least 10% by weight of $CO_2$ to the synthesis gas stream.

7. The process of claim 6, wherein adding at least a portion of the $CO_2$-containing stream into the synthesis gas stream comprises adding from 15% to 22% by weight of $CO_2$ to the synthesis gas stream.

8. The process of claim 1, wherein adding at least a portion of the separated $CO_2$-containing stream comprises adding at least 90% of the separated $CO_2$-containing stream is added to the synthesis gas stream.

9. The process of claim 1, wherein the carbon oxide conversion catalyst is a nickel containing catalyst.

10. The process of claim 1, wherein the carbon oxide conversion catalyst comprises at least one active metal or metal oxide of Group 6 or Group 8-10 of the Periodic Table of the Elements.

11. The process of claim 1, wherein the olefin forming catalyst is a molecular sieve catalyst.

12. The process of claim 11, wherein the molecular sieve catalyst is a silicoaluminophosphate molecular sieve.

13. The process of claim 1, further comprising contacting the olefin stream with a polyolefin forming catalyst to form a polyolefin.

14. The process of claim 1, further comprising purifying the at least a portion of the separated $CO_2$-containing stream prior to adding the at least a portion of the separated $CO_2$-containing stream to the synthesis gas stream.

15. The process of claim 14, wherein purifying the at least a portion of the separated $CO_2$-containing stream comprises removing at least a portion of the sulfur-containing compounds in the separated $CO_2$-containing stream.

16. The process of claim 15, wherein the purified $CO_2$-containing stream comprises 10 ppm or less of $H_2S$.

17. The process of claim 1, further comprising adding a second portion of the separated $CO_2$-containing stream to the second natural gas stream prior to forming the synthesis gas.

18. A process for forming an olefin stream, the process comprising:
   (a) separating a $CO_2$-containing stream from a natural gas stream, the natural gas stream comprising at least 5 mol % $CO_2$ and the $CO_2$-containing stream comprising at least 75% $CO_2$ by weight;
   (b) adding at least a portion of the separated $CO_2$-containing stream into a second natural gas stream;
   (c) forming a synthesis gas stream from the second natural gas stream;
   (d) contacting the formed synthesis gas stream with a carbon oxide conversion catalyst to form a methanol composition comprising:
      i. at least 50 wt % and less than 99.85 wt % methanol, based on total weight of the methanol composition,
      ii. greater than 10 wppm and not greater than 15 wt % ethanol, based on total weight of the methanol composition, and
      iii. greater than 10 wppm and not greater than 15 wt % acetaldehyde, based on total weight of the methanol composition; and (e) contacting the methanol composition with an olefin forming catalyst to form an olefin stream comprising greater than 65 wt % ethylene and propylene.

19. The process of claim 18, wherein the second natural gas stream is derived from the first natural gas stream.

20. The process of claim 18, wherein forming a synthesis gas stream comprises forming a synthesis gas stream having a value of a ratio M of at least 2.0, the ratio M being defined as $$M=([CO]+[H_2])/([CO]+[CO_2])$$

where [CO], [H$_2$], and [CO$_2$] represent the molar concentration of each compound.

21. The process of claim 20, wherein the value of M for the synthesis gas stream is from 2.05 to 2.5.

22. The process of claim 18, wherein adding at least a portion of the separated CO$_2$-containing stream into the second natural gas stream comprises adding at least 10% by weight of CO$_2$ to the second natural gas stream.

23. The process of claim 22, wherein adding at least a portion of the separated CO$_2$-containing stream into the second natural gas stream comprises adding from 15% to 22% by weight of CO$_2$ to the second natural gas stream.

24. The process of claim 18, wherein adding at least a portion of the separated CO$_2$-containing stream comprises adding at least 90% of the separated CO$_2$-containing stream is added to the second natural gas stream.

25. The process of claim 18, wherein the carbon oxide conversion catalyst is a nickel containing catalyst.

26. The process of claim 18, wherein the carbon oxide conversion catalyst comprises at least one active metal or metal oxide of Group 6 or Group 8-10 of the Periodic Table of the Elements.

27. The process of claim 18, wherein the olefin forming catalyst is a molecular sieve catalyst.

28. The process of claim 27, wherein the molecular sieve catalyst is a silicoaluminophosphate molecular sieve.

29. The process of claim 18, further comprising contacting the olefin stream with a polyolefin forming catalyst to form a polyolefin.

30. The process of claim 18, further comprising purifying the at least a portion of the separated CO$_2$-containing stream prior to adding the at least a portion of the separated CO$_2$-containing stream to the second natural gas stream.

31. The process of claim 30, wherein purifying the at least a portion of the separated CO$_2$-containing stream comprises removing at least a portion of the sulfur-containing compounds in the separated CO$_2$-containing stream.

32. The process of claim 31, wherein the purified CO$_2$-containing stream comprises 10 ppm or less of H$_2$S.

33. The process of claim 18, further comprising adding a second portion of the separated CO$_2$-containing stream to the synthesis gas stream prior to contacting the synthesis gas stream with the carbon oxide conversion catalyst.

34. The process of claim 18, further comprising performing a hydrodesulfurization process on the second natural gas stream after adding the at least a portion of the separated CO$_2$-containing stream.

* * * * *